United States Patent
Helvick et al.

(10) Patent No.: US 11,376,440 B2
(45) Date of Patent: Jul. 5, 2022

(54) METHOD FOR MANAGING A WIRELESS COMMUNICATION BETWEEN AN IMPLANTABLE MEDICAL DEVICE AND AT LEAST TWO EXTERNAL DEVICES

(71) Applicant: BIOTRONIK SE & CO. KG, Berlin (DE)

(72) Inventors: Richard Helvick, Portland, OR (US); Rainer Joerg Grosskopf, Portland, OR (US); David Kosokowsky, Lake Oswego, OR (US); Wells Ian Matthews, Beaverton, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 301 days.

(21) Appl. No.: 16/813,890

(22) Filed: Mar. 10, 2020

(65) Prior Publication Data
US 2020/0298011 A1    Sep. 24, 2020

Related U.S. Application Data

(60) Provisional application No. 62/819,714, filed on Mar. 18, 2019.

(51) Int. Cl.
| | |
|---|---|
| *A61N 1/372* | (2006.01) |
| *A61N 1/36* | (2006.01) |
| *H04W 76/30* | (2018.01) |
| *H04W 4/80* | (2018.01) |
| *H04W 8/00* | (2009.01) |

(52) U.S. Cl.
CPC ...... *A61N 1/37223* (2013.01); *A61N 1/36062* (2017.08); *A61N 1/37247* (2013.01); *H04W 4/80* (2018.02); *H04W 8/005* (2013.01); *H04W 76/30* (2018.02)

(58) Field of Classification Search
CPC ............ A61N 1/37223; A61N 1/37235; A61N 1/37247; A61N 1/37254; A61N 1/37264; A61N 1/3727; A61N 1/37276; A61N 1/37252; A61N 1/37288; H04W 8/005; H04W 8/02; H04W 8/04; H04W 8/06; H04W 48/16
See application file for complete search history.

(56) References Cited

U.S. PATENT DOCUMENTS

| | | |
|---|---|---|
| 2007/0060980 A1 | 3/2007 | Strother et al. |
| 2017/0312530 A1 | 11/2017 | Schilling et al. |
| 2018/0021589 A1 | 1/2018 | Wu et al. |

*Primary Examiner* — Paula J Stice
(74) *Attorney, Agent, or Firm* — Laurence A. Greenberg; Werner H. Stemer; Ralph E. Locher

(57) ABSTRACT

A method for managing a wireless communication between an implantable medical device and at least two external devices includes associating the implantable medical device with a first external device so as to enable communication between the first external device and the implantable medical device via a wireless connection, and activating a search mode of the implantable medical device. In the search mode, the implantable medical device wirelessly sends out an advertising message that indicates its availability for association with at least a second external device. A blocking mode of the first external device is activated in response to the activation of the search mode of the implantable medical device. In the blocking mode, the first external device is disconnected from the implantable medical device and does not attempt to connect with the implantable medical device.

15 Claims, 2 Drawing Sheets

METHOD FOR MANAGING A WIRELESS COMMUNICATION BETWEEN AN IMPLANTABLE MEDICAL DEVICE AND AT LEAST TWO EXTERNAL DEVICES

CROSS-REFERENCE TO RELATED APPLICATION

This application claims the benefit, under 35 U.S.C. § 119(e), of U.S. Provisional Patent Application No. 62/819,714, filed Mar. 18, 2019; the prior application is herewith incorporated by reference in its entirety.

BACKGROUND OF THE INVENTION

Field of the Invention

The present invention generally relates to a method for managing a wireless communication between an implantable medical device and at least two external devices. The present invention also relates to a system including an implantable medical device, a first external device, and a second external device. Further, the present invention relates to an external device for wirelessly communicating with an implantable medical device.

Some current configurations of communication systems for implantable medical devices rely on an external programmer continuously maintaining a wireless connection with at least a component of the implantable medical device when the latter is implanted in the human body. For example, in a known communication system configured for spinal cord stimulation (SCS), an external programmer, such as a so-called patient remote, continuously maintains a Bluetooth low energy (BLE) connection with an implanted pulse generator of the SCS system. Whenever the wireless connection is dropped, the external programmer will aggressively attempt to reconnect to the implanted pulse generator. Such a configuration allows for a relatively low power demand while at the same time ensuring a low communication latency.

While it is usually beneficial for an external programmer to maintain a connection to its associated implantable pulse generator whenever it is in range, that may result in scenarios where the implantable pulse generator appears unavailable to additional external programmers when a user intends to associate a different external programmer. That unavailability of the implantable pulse generator may appear to the user as a communication issue, thus resulting in a poor user experience. In a worst case scenario, a clinician could believe that the implantable pulse generator is nonresponsive and (erroneously) determine that an explant is needed.

For example, a clinician may want to connect a clinician's programmer to the implanted pulse generator in order to carry out a follow-up session. Conventionally, in such a situation, the user, i.e., the patient or clinician, needs to manually disable the wireless connection of the patient remote to the implanted pulse generator before the wireless connection between the clinician's programmer and the implanted pulse generator can be established. Hence, the problem arises that it may be impossible to connect the second external programmer (e.g., the clinician's programmer) in case the location of the first external programmer (e.g., the patient remote) is currently unknown or in case it is otherwise physically inaccessible.

Approaches exist to provide for the possibility of a simultaneous communication between an implanted pulse generator and two external devices, as known, for example, from U.S. Patent Application Publication No. 2017/0312530 A1. However, in the case of medical therapy implants, such a configuration generally comes with the inconvenience that it introduces complexity in the implantable pulse generator, which is subject to strict resource constraints. Further, a solution wherein the implanted pulse generator is configured to handle two simultaneous wireless connections (namely, with two distinct external devices) could cause confusion for the user in case the two external devices make competing changes to the therapy settings of the implanted pulse generator.

SUMMARY OF THE INVENTION

It is accordingly an object of the invention to provide a method for managing a wireless communication between an implantable medical device and at least two external devices, which overcomes the hereinafore-mentioned disadvantages and difficulties of the heretofore-known methods of this general type. For example, it is desirable to eliminate the potential communication issues described above and to thus provide a better user experience. In particular, the desired solution should allow for connecting a second external device to the implanted medical device also in situations, wherein a first external device that is already associated with the implanted medical device is currently inaccessible. Further, there is a desire for providing a system and an external device that support such a method.

Such desires are addressed, according to a first aspect of the instant invention, by a method for managing a wireless communication between an implantable medical device and at least two external devices, wherein the method includes at least the following steps: associating the implantable medical device with a first external device so as to enable communication between the first external device and the implantable medical device via the wireless connection; activating a search mode of the implantable medical device, wherein, in the search mode, the implantable medical device wirelessly sends out an advertising message that indicates its availability for association with at least a second external device; and activating a blocking mode of the first external device in response to the activation of the search mode of the implantable medical device, wherein, in the blocking mode, the first external device is disconnected from the implantable medical device and does not attempt to connect with the implantable medical device.

Hence, it is proposed to cause the currently associated first external device to automatically stop its (re-)connection attempts so as to allow for the second external device to be associated—and then connected—with the implantable medical device. Drawbacks of currently known systems can thus be avoided, for example, by providing a fallback solution in case the external device that is currently connected to the implantable medical device is in an unknown location or otherwise inaccessible, or in case the user forgets to disable connections. In such a situation, the present invention allows for the association—and then connection—of the second external device in spite of the current inaccessibility of the first external device. For example, it may thus be possible for a clinician to carry out a follow-up session on the implantable medical device.

In an exemplary embodiment, the implantable medical device is an implanted pulse generator, e.g., of an SCS system. Further, in this embodiment, the first external device may be a patient remote, whereas the second external device may be, for example, a clinician's programmer used by a clinician for carrying out a follow-up session. Such a patient remote and such a clinician's programmer are two distinct types of external programmers. Thus, the method according to the first aspect of the present invention may, for example, enable a smooth handoff from the patient remote to the clinician's programmer of an SCS system so as to facilitate a follow-up session.

Regarding the association step of the method as outlined above, it should be noted that "association" of an external device with the implantable medical device means that the respective external device and the implantable medical device have identified each other as intended communication partners for the wireless communication. Normally, i.e. unless the external device is in the blocking mode, the external device will aggressively attempt to maintain a wireless connection that enables the communication with the associated implantable medical device. In other words, if the external device is associated with the implanted medical device, and as long as it is not in the blocking mode, it will immediately begin searching for the implantable medical device whenever the connection is dropped and reconnect to the implanted medical device as soon as implanted medical device is found. However, while in the blocking mode, the first external device will not attempt to connect to its currently associated implantable medical device, thus facilitating the handoff from the first external device to the second external device. Correspondingly, in an embodiment, the method includes, as a further step, associating the second external device with the implantable medical device.

Referring to the search mode mentioned above, it should be noted that, generally, when the implantable medical device is not connected, but associated with an external device, the implantable medical device will advertise to facilitate quick discovery by the associated external device when it is within a range. By contrast, if the disconnected implantable medical device is not associated with an external device, it does not advertise unless the implantable medical device is in the search mode.

In an embodiment, activating the search mode may include placing a magnet close to the implantable medical device. For example, in case the medical device is implanted in a human body, the search mode may be activated by using the magnetic interaction between a magnet that is positioned in contact with or close to the skin of the patient in the vicinity of the implanted medical device. The implantable medical device may include devices for sensing the magnetic interaction and may automatically activate its search mode in response to receiving a magnetic field of a certain minimum strength. Further, it may be provided that the search mode is activated only if the magnet is applied at least for a predetermined time interval, such as, e.g., 10 seconds. Thus, an unintended activation of the search mode by an accidental brief exposure to the magnetic field may be prevented. The implantable medical device may, for example, include a processor unit configured for activating the search mode in dependence on a perceived magnetic field.

Further, in an embodiment, the blocking mode of the first external device may be automatically activated in response to the reception of an advertising message by the first external device. For example, to this end, the advertising message may indicate whether the search mode of the implantable medical device is active. This may be attained, for example, by including information regarding a search mode status of the implantable medical device in the advertising message, such as, e.g., a search mode status that indicates whether or not the search mode is active. Thus, if the first external device receives an advertising message for its associated implantable medical device, the first external device will check the indicated search mode status. If the search mode status is "active," the first external device will automatically enter the blocking mode.

In an embodiment, it may be provided that a first user interface of the first external device indicates the activation of the blocking mode to the user. In this way, it may be clearly communicated to both the patient and the clinician which external programmer—the first external device in the form of the patient remote or the second external device in the form of the clinician's programmer—is currently in control. For example, the first user interface may include indication devices, such as a display, one or more LEDs, or the like, for being able to convey such information to the user. Further, the first user interface may include input devices, such as, e.g., one or more buttons and/or knobs, a keyboard, a touchscreen, or the like, which allow for the user to input parameters and/or commands to the first external device. For example, the user may use the first user interface to switch the first external device from the blocking mode to a connected mode, in which case the first external device will automatically (re-)connect to the implantable medical device. In other words, the method according to the present invention may further include exiting the blocking mode responsive to a user interaction via a first user interface of the first external device, e.g., after the association between the implantable medical device and the second external device has ended.

Further, in an embodiment, the first external device may exit the blocking mode automatically upon expiration of a timer. For example, it may be provided that a timer is started in response to the activation of the blocking mode and that the first external device automatically exits the blocking mode responsive to the expiration of the timer. For example, such a timer may be implemented in the first external device. In this way, it may be ensured that the first external device can reconnect to the implantable medical device after a certain time. For example, the timer may be configured such that it expires only after a time period that corresponds at least to the typical duration of a follow-up procedure.

In a further variant embodiment, the advertising message may include, in addition to the search mode status, information regarding the number of external devices the implantable medical device is currently associated with. For example, the first external device may continue to monitor advertising messages during the blocking mode and may automatically exit the blocking mode responsive to receiving an advertising message indicating that the implantable medical device is not in the search mode (search mode status "not active") and that the implantable medical device is currently associated with only one external device. In such a situation, there is no reason to uphold the blocking mode any longer and it may thus be advantageous if the first external device automatically exits the blocking mode so as to enable (re-)connection with the implantable medical device.

Similarly to what has been described above with regards to the first user interface, the second external device may also include a (second) user interface, which allows for conveying information to the user (e.g. the clinician) and/or for inputting user inputs, such as parameters or commands. For example, in an embodiment, such a second user interface of the second external device may indicate the availability of the implantable medical device for association with the second external device responsive to receiving an advertising message indicating the search mode of the implantable medical device. The user may then use the second user interface to command the second external device to connect with the implantable medical device and start the association process between the implantable medical device and the second external device. Thus, the method according to the present invention may further include associating the second external device with the implantable medical device responsive to a user interaction via the second user interface.

The wireless communication between the implantable medical device and the first and second external device may be based on a protocol for short range wireless connection, such as the Bluetooth low energy (BLE) protocol, for example. Such a configuration may provide for relatively modest power demands while allowing a BLE connection, e.g., between an external programmer and an implanted pulse generator of an SCS system, to be continuously maintained.

According to a second aspect of the present invention, a system including an implantable medical device, a first external device, and a second external device, is provided. The first external device is configured for entering into association with the implantable medical device so as to enable communication between the first external device and the implantable medical device via a wireless connection. The implantable medical device is configured for entering a search mode of the implantable medical device while being associated with the first external device, wherein, in the search mode, the implantable medical device wirelessly sends out an advertising message that indicates its availability for association with at least a second external device. The first external device is further configured for automatically entering a blocking mode of the first external device in response to the activation of the search mode of the implantable medical device, wherein, in the blocking mode, the first external device is disconnected from the implantable medical device and does not attempt to connect with the implantable medical device.

According to a third aspect of the present invention, an external device for wirelessly communicating with an implantable medical device is configured for entering into association with the implantable medical device so as to enable communication between the first external device and the implantable medical device via a wireless connection; and automatically activating a blocking mode of the first external device in response to receiving an advertising message from the associated implantable medical device, wherein the advertising message indicates that the implantable medical device has entered a search mode, and wherein, in the blocking mode, the first external device is disconnected from the implantable medical device and does not attempt to connect with the implantable medical device.

The system according to the second aspect of the present invention and the external device according to the third aspect of the present invention may be used for carrying out the method of the first aspect of the present invention. In other words, the components of the system according to the second aspect and the external device according to the third aspect may be configured for carrying out corresponding method steps. For example, the external device of the third aspect may correspond to the first external device referred to in connection with the method according to the first aspect. Correspondingly, what has been described above and will be described in the following with reference to the method of the first aspect, may analogously apply to the system and the external device according to the second and third aspects, and vice versa.

Other features which are considered as characteristic for the invention are set forth in the appended claims.

Although the invention is illustrated and described herein as embodied in a method for managing a wireless communication between and implantable medical device and at least two external devices, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1A:
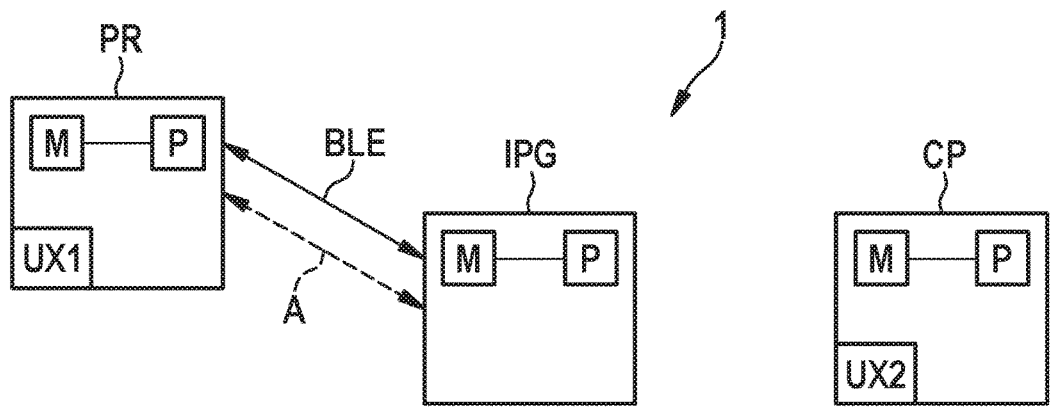
FIGS. 1A and 1B are each block diagrams of a system including an implantable medical device, a first external device, and a second external device.

Subsequently, embodiments of the invention shall be described in detail with reference to the drawings. In the drawings, like reference numerals designate like structural elements.

It is to be noted that the embodiments are not limiting for the invention, but merely represent illustrative examples.

In the present invention, a method for managing a wireless communication between an implantable medical device and at least two external devices is proposed. Further, a corresponding system as well as an external device, which may enable such a method, are proposed.

Figure 1B:
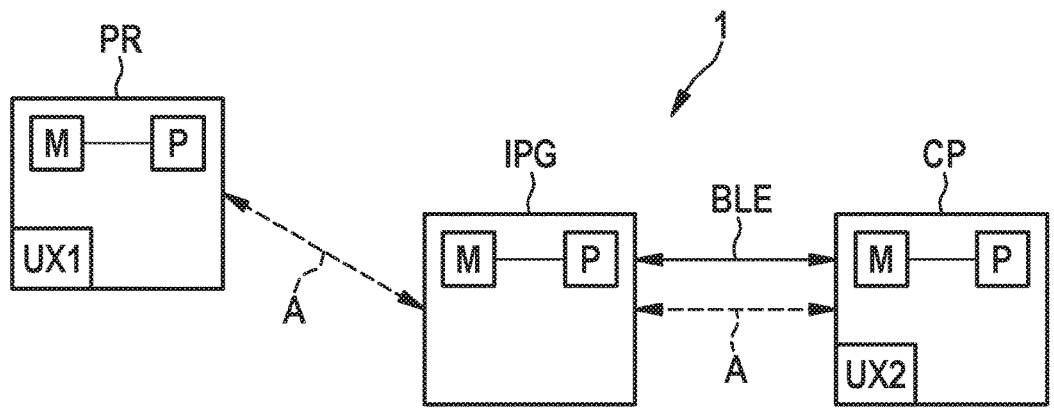

Referring now to the figures of the drawings in detail and first, particularly, to each of FIGS. 1A and 1B thereof, there is seen a block diagram of a system 1 including an implantable medical device IPG, a first external device PR and a second external device CP. In this exemplary embodiment, the implantable medical device IPG is a pulse generator for spinal cord stimulation (SCS) that is implanted in the body of a patient. The first external device PR is a patient remote to be carried by the patient. In normal use, the patient remote PR continuously maintains a wireless connection BLE based on the Bluetooth Low Energy protocol with the implanted pulse generator IPG. The patient remote PR has a first user interface UX1, which allows the patient, e.g., to retrieve information on the operation of the pulse generator and input control commands.

As a prerequisite for establishing and maintaining the wireless connection BLE (indicated with a solid arrow in FIG. 1A), the patient remote PR needs to be associated with the implantable pulse generator IPG. In FIG. 1A, an association A between the patient remote PR and the implantable pulse generator IPG is schematically indicated by a dashed arrow. In this context, association means that the patient remote PR and the implantable generator IPG have mutually recognized (and possibly authenticated) each other as intended communication partners for the communication via the wireless connection BLE.

For example, each of the patient remote PR and the implantable pulse generator IPG may include a respective processor unit P and a memory unit M that interacts with the processor unit, wherein, as a consequence of the association A, an identifier (e.g., in the form of a serial number and/or a communication certificate) of the associated pulse generator IPG may be stored in the memory unit M of the patient remote, and vice versa. For example, such an association A may be established by using a handshake procedure, as is generally well known in the art and will therefore not be described in further detail.

While associated with the implantable pulse generator IPG, the patient remote PR normally will aggressively attempt to reconnect to the implantable pulse generator IPG anytime the wireless connection BLE is interrupted. FIG. 1A shows a situation corresponding to such a normal operation of the system 1.

Further, the system 1 includes, in addition to the implantable pulse generator IPG and the patient remote PR, a clinician's programmer CP. The clinician's programmer CP is another external programmer, which, similarly to the patient remote PG, has a (second) user interface UX2. The clinician's programmer CP is supposed to be operated by a clinician, for example, during a follow-up session, during which the operation of a SCS system may be checked and, as necessary, adjusted by the clinician.

When the patient has a follow-up session with the clinician, a handoff from the patient remote PR to the clinician's programmer CP needs to be effected. The handoff may correspond to a transition from the normal use situation as schematically illustrated in FIG. 1A to the follow-up situation as schematically illustrated in FIG. 1B.

As illustrated in FIG. 1B, in the follow-up situation, the implantable pulse generator IPG is associated and wirelessly connected with the clinician's programmer CP so as to enable access of the clinician to the functions of the implantable pulse generator IPG. The patient remote PR is disconnected from the implantable pulse generator IPG while still maintaining its association A with the implantable pulse generator IPG. Normally, the patient remote PR would try to reestablish the wireless communication BLE with the associated implantable pulse generator IPG. Therefore, according to a conventional approach, in a follow-up situation as exemplarily depicted in FIG. 1B, the patient or the clinician may use the first user interface UX1 on the patient remote PR to activate a disconnected mode, in which the patient remote PR is and remains disconnected from the implantable pulse generator IPG. The clinician can then use the second user interface UX2 on the clinician's programmer to connect and associate the clinician's programmer CP to the implantable pulse generator IPG. At this point, the clinician may use the second user interface UX2 on the clinician's programmer CP to perform the follow-up procedures.

However, a situation may arise, wherein an associated and connected external program, such as the patient remote PR as illustrated in FIG. 1A, is currently not accessible when the user desires to connect a second external programmer, such as the clinician's programmer CP, to the implantable medical device IPG. For example, referring to the embodiment of FIG. 1A, the patient may be in the clinician's office for a follow-up procedure and the clinician may wish to connect the clinician's programmer to the implantable pulse generator IPG that is implanted in the patient's body. However, the patient remote PR that is associated with and connected to the implantable pulse generator IPG may be currently physically inaccessible to the patient or clinician. In the following, it will be described how the present invention allows for carrying out the follow-up procedure in such a scenario.

Figure 2A:
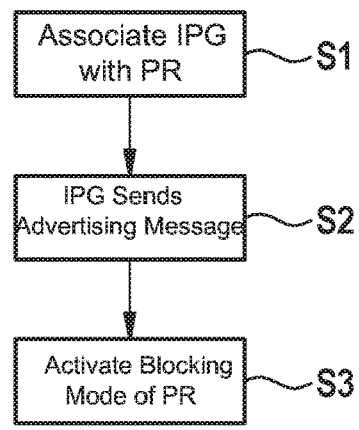
FIG. 2A is a flow diagram of a method for managing a wireless communication between the implantable device and the first and second external devices of FIGS. 1A and 1B.

FIG. 2A is a schematic illustration of a method for managing the wireless communication between the implantable pulse generator IPG, the patient remote PR, and the clinician's programmer CP in a situation, wherein the patient remote PR is initially associated and connected, but not accessible to the clinician or the patient.

In the step S1, the implantable pulse generator IPG is associated with the patient remote PR so as to enable communication between the patient remote PR and the implantable pulse generator IPG via the wireless connection BLE.

In the step S2, a search mode of the implantable pulse generator IPG is activated, wherein, in the search mode, the implantable pulse generator IPG wirelessly sends out an advertising message that indicates its availability for association with at least the clinician's programmer CP. It should, of course, be understood that the advertising message may also indicate availability for further external devices, such as further external programmers.

In the step S3, a blocking mode of the patient remote PR is activated in response to the activation of the search mode of the implantable pulse generator IPG, wherein, in the blocking mode, the patient remote PR is disconnected from the implantable pulse generator IPG and does not attempt to connect with the implantable pulse generator IPG.

Figure 2B:
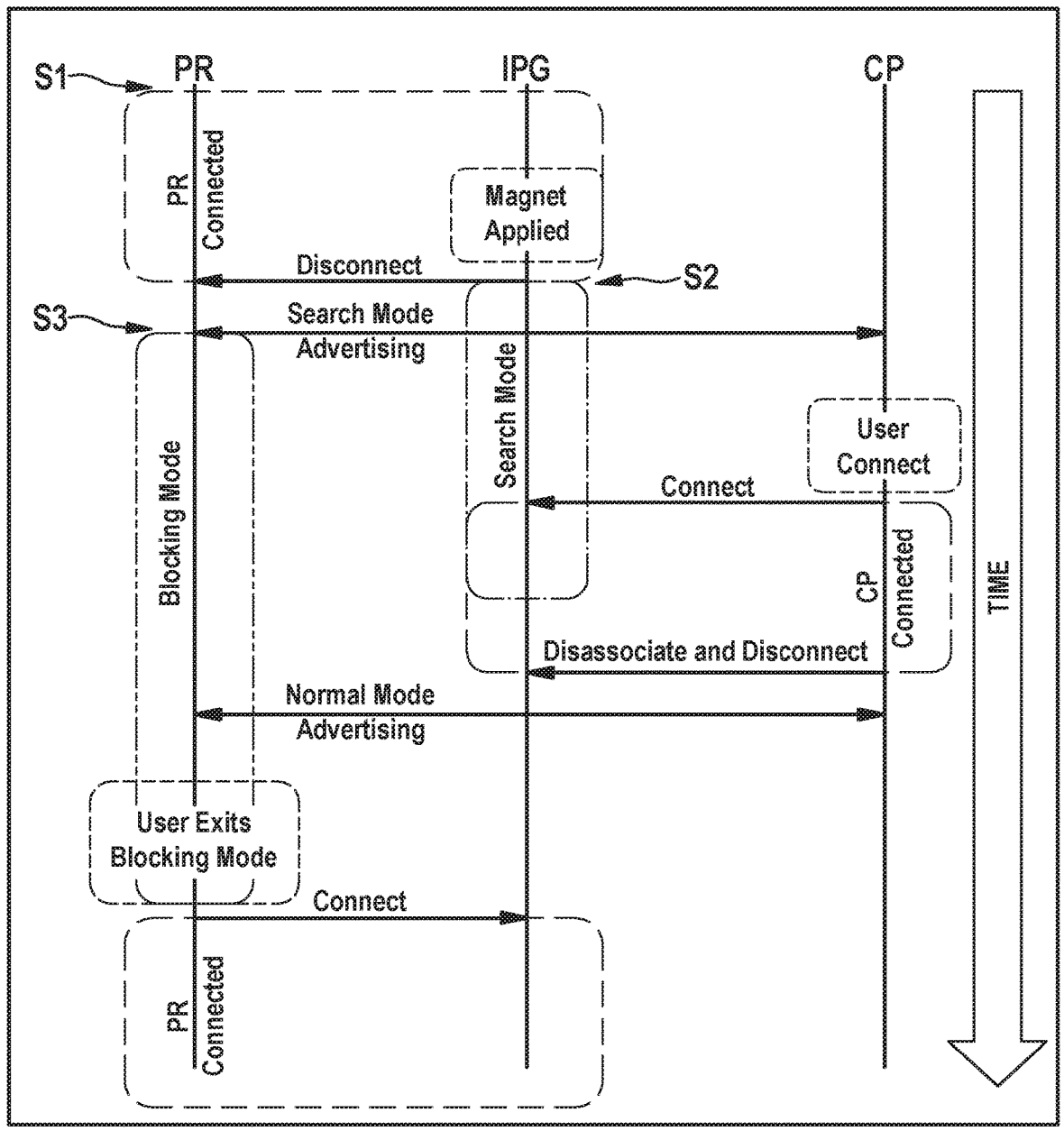
FIG. 2B is a more detailed flow diagram of an exemplary embodiment of the method of FIG. 2A.

FIG. 2B shows a more detailed schematic illustration of an exemplary embodiment of the method according to the present invention. In FIG. 2B, a respective timeline (pointing from top to bottom) for each of the patient remote PR, the implantable pulse generator IPG and the clinician's programmer CP, is schematically depicted. The timelines indicate the interactions and connections between the different components of the system 1 as well as the user interaction at each stage of the process.

In the beginning, the patient remote is connected and associated (step S1) with the implantable pulse generator IPG, in accordance with the normal-use situation depicted in FIG. 1A. The clinician then applies a magnet to the implantable pulse generator IPG, thereby causing the implantable pulse generator IPG to enter its search mode (step S2). For example, the magnet may be placed on or close to the skin of the patient in the vicinity of the implanted pulse director IPG for a predetermined minimum period of time, such as, e.g. 10 seconds, so as to activate the search mode.

Once in the search mode, the implantable pulse generator IPG begins advertising by wirelessly sending out an advertising message that indicates its availability for association, e.g., with the clinician's programmer CP. The advertising message includes information regarding the search mode status of the implantable pulse generator IPG. Specifically, the search mode status included in the advertising message may indicate that the search mode is currently active. The patient remote PR receives the advertising message from the implantable pulse generator IPG and decodes the advertising message.

Recognizing that the search mode status conveyed with the advertising message is set to "active" for the implantable pulse generator IPG, the patient remote PR automatically enters a blocking mode (step S3). In the blocking mode, the patient remote PR is and remains disconnected from the implantable pulse generator IPG. Specifically, during the blocking mode, the patient remote PR is inhibited from attempting to reconnect with the implantable pulse generator IPG. The first user interface UX1 of the patient remote PR indicates the activation of the blocking mode to the patient.

The clinician's programmer CP also receives and decodes the advertising message from the implantable pulse generator IPG. Recognizing, by using the search mode status "active" conveyed with the advertising message, that the advertising message stems from an implantable pulse generator IPG in its search mode, the clinician's programmer CP informs the user via the second user interface UX2 that an implantable pulse generator IPG is currently available for association. In other words, in response to receiving the advertising message from the implantable pulse generator IPG, the second user interface UX2 of the clinician's programmer CP indicates the availability of the implantable pulse generator IPG for association with the clinician's programmer CP. The clinician then uses the second user interface UX2 on the clinician's programmer CP to connect the clinician's programmer CP to the implantable pulse generator IPG and begin the association process. Thus, the clinician's programmer CP is associated with the implantable pulse generator IPG responsive to a user interaction via the second user interface UX2 on the clinician's programmer CP. As a result, the clinician's programmer CP is associated and wirelessly connected with the implantable pulse generator IPG. The clinician can then use the clinician's programmer CP to perform the necessary follow-up procedures. Once the follow-up is completed, the clinician's programmer CP is disassociated and disconnected from the implantable pulse generator IPG. At this point, the implantable pulse generator IPG is no longer in its search mode, but in a normal mode, in which it may advertise with the search mode status "inactive."

The patient or clinician can use the first user interface UX1 on the patient remote PR to exit the blocking mode once the follow-up is completed. This is to say that the patient remote PR exits the blocking mode responsive to a user interaction via the first user interface UX1 after the association between the implantable pulse generator IPG and the clinician's programmer CP has ended. Alternatively, the patient remote PR may include a timer, which automatically starts when the blocking mode is activated, wherein patient remote PR may be configured to automatically exit the blocking mode when the timer expires. The duration of the timer may be chosen so as to cover at least a typical duration of a follow-up procedure.

In a further variant, the advertising message sent out by the implantable pulse generator IPG includes, in addition to the search mode status, information regarding the number of external devices the implantable pulse generator IPG is currently associated with. In this case, the patient remote PR may automatically exit the blocking mode responsive to receiving an advertising message indicating that the implantable pulse generator IPG is currently not in the search mode and that the implantable pulse generator IPG is currently associated with only one external device.

Finally, when the patient remote PR has exited its blocking mode, it will scan for the implantable pulse generator IPG and reconnect once it discovers the implantable pulse generator IPG.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

1 System
BLE Wireless connection
CP Second external device/Clinician's programmer
IPG Implantable medical device/Implantable pulse generator
M Memory unit
P Processor unit
PR First external device/Patient remote
S1-S3 Method steps
UX1 First user interface
UX2 Second user interface

The invention claimed is:

1. A method for managing a wireless communication between an implantable medical device and at least first and second external devices, the method comprising the following steps:
   associating the implantable medical device with the first external device so as to enable communication between the first external device and the implantable medical device via a wireless connection;
   activating a search mode of the implantable medical device, and wirelessly sending out an advertising message from the implantable medical device in the search mode indicating an availability of the implantable medical device for association with at least the second external device; and
   activating a blocking mode of the first external device in response to the activation of the search mode of the implantable medical device, and in the blocking mode disconnecting the first external device from the implantable medical device and not attempting a connection between the first external device and the implantable medical device.

2. The method according to claim 1, which further comprises associating the second external device with the implantable medical device.

3. The method according to claim 1, which further comprises carrying out the step of activating the search mode by placing a magnet close to the implantable medical device.

4. The method according to claim 1, which further comprises automatically activating the blocking mode in response to reception of the advertising message by the first external device.

5. The method according to claim 1, which further comprises including in the advertising message information regarding a search mode status of the implantable medical device.

6. The method according to claim 5, which further comprises additionally including in the advertising message information regarding a number of external devices with which the implantable medical device is currently associated.

7. The method according to claim 6, which further comprises causing the first external device to automatically exit the blocking mode responsive to receiving an advertising message indicating that the implantable medical device is not in the search mode and is currently associated with only one external device.

8. The method according to claim 1, which further comprises starting a timer in response to the activation of the blocking mode, and causing the first external device to automatically exit the blocking mode responsive to an expiration of the timer.

9. The method according to claim 1, which further comprises using a first user interface of the first external device to indicate the activation of the blocking mode.

10. The method according to claim 1, which further comprises, in response to receiving the advertising message, using a second user interface of the second external device to indicate the availability of the implantable medical device for association with the second external device.

11. The method according to claim 10, which further comprises associating the second external device with the implantable medical device responsive to a user interaction via the second user interface.

12. The method according to claim 11, which further comprises exiting the blocking mode responsive to a user interaction via a first user interface of the first external device after the association between the implantable medical device and the second external device has ended.

13. The method according to claim 1, which further comprises basing the wireless communication on the Bluetooth Low Energy protocol.

14. A system, comprising:
an implantable medical device, a first external device, and a second external device;
said first external device configured for entering into association with said implantable medical device to enable communication between said first external device and said implantable medical device via a wireless connection;
said implantable medical device configured for entering a search mode of said implantable medical device while being associated with said first external device, in said search mode, said implantable medical device wirelessly sending out an advertising message indicating an availability of said implantable medical device for association with at least said second external device; and
said first external device configured for automatically entering a blocking mode of said first external device in response to an activation of said search mode of said implantable medical device, in said blocking mode, said first external device being disconnected from said implantable medical device and not attempting to connect with said implantable medical device.

15. A medical system, comprising:
an external device for wirelessly communicating with an implantable medical device, said external device being configured for:
entering into association with the implantable medical device to enable communication between the external device and the implantable medical device via a wireless connection; and
automatically activating a blocking mode of the external device in response to receiving an advertising message from the associated implantable medical device, the advertising message indicating entry of the implantable medical device into a search mode, and, in the blocking mode, the external device being disconnected from the implantable medical device and not attempting to connect with the implantable medical device.

* * * * *